United States Patent
Hull (10) Patent No.: US 11,219,708 B2
(45) Date of Patent: Jan. 11, 2022

(54) FISTULA CANNULA

(71) Applicant: Covidien LP, Mansfield, MA (US)

(72) Inventor: Les Hull, Attleboro, MA (US)

(73) Assignee: COVIDIEN LP, Mansfield, MA (US)

( * ) Notice: Subject to any disclaimer, the term of this patent is extended or adjusted under 35 U.S.C. 154(b) by 146 days.

(21) Appl. No.: 16/270,962

(22) Filed: Feb. 8, 2019

(65) Prior Publication Data

US 2019/0328954 A1    Oct. 31, 2019

Related U.S. Application Data (60) Provisional application No. 62/664,505, filed on Apr. 30, 2018.

(51) Int. Cl.
| | | |
|---|---|---|
| *A61M 25/06* | (2006.01) | |
| *A61M 1/36* | (2006.01) | |
| *A61M 1/14* | (2006.01) | |
| *A61M 39/02* | (2006.01) | |

(52) U.S. Cl.
CPC ............ *A61M 1/3655* (2013.01); *A61M 1/14* (2013.01); *A61M 39/0247* (2013.01); *A61M 25/0606* (2013.01); *A61M 25/0631* (2013.01); *A61M 2039/0258* (2013.01); *A61M 2039/0291* (2013.01)

(58) Field of Classification Search
CPC ........ A61M 1/3655; A61M 2039/0258; A61M 25/0606; A61M 25/0631
See application file for complete search history.

(56) References Cited

U.S. PATENT DOCUMENTS

| | | |
|---|---|---|
| 6,537,253 B1 | 3/2003 | Haindl |
| 7,335,187 B2 | 2/2008 | Altman |
| 7,951,115 B2* | 5/2011 | Altman ............... A61M 1/3661 604/164.01 |
| 2003/0083621 A1 | 5/2003 | Shaw et al. |
| 2016/0296728 A1* | 10/2016 | Smith ............... A61M 25/0631 |
| 2020/0261266 A1* | 8/2020 | Bley .................... A61K 47/543 |

OTHER PUBLICATIONS

Extended Search Report from counterpart European Application No. 19171686.9, dated Oct. 1, 2019, 8 pp.
Response to Extended Search Report dated Nov. 11, 2019, from counterpart European Application No. 19171686.9, filed May 6, 2020, 10 pp.

* cited by examiner

*Primary Examiner* — Deanna K Hall
(74) *Attorney, Agent, or Firm* — Shumaker & Sieffert, P.A.

(57) ABSTRACT

In some examples, a device, which may be used to access vasculature or another hollow anatomical structure of a patient, includes a housing, a cannula mechanically coupled to a housing distal end, and a needle configured to be locked in a deployed configuration in which the needle extends within a cannula lumen and protrudes from the cannula distal end. The needle is configured to slide proximally through the cannula lumen from the deployed configuration into a retracted configuration in which at least a portion of the needle is within a housing lumen. The device further includes at least one needle guide configured to maintain the needle along a path in the housing lumen substantially parallel to the needle guide when the needle moves between the deployed configuration and the retracted configuration.

32 Claims, 6 Drawing Sheets

FISTULA CANNULA

CROSS-REFERENCE TO RELATED APPLICATION

This application claims the benefit of and priority to U.S. Provisional Patent Application No. 62/664,505 filed Apr. 30, 2018, the entire disclosure of which is incorporated by reference herein.

TECHNICAL FIELD

The present disclosure relates to, in some examples, a device that can be used to access vasculature of a patient.

BACKGROUND

Devices such as catheters or fistula cannulas may be used to gain access to vasculature of a patient, for example, for hemodialysis. Such a device may include a needle used to facilitate introduction of a portion of the device into a blood vessel and a cannula or other tubular structure through which fluid may be introduced into or withdrawn from the vessel. In some cases, the device may be left in a vessel during a treatment or procedure, and may be subsequently withdrawn from the vessel.

SUMMARY

The present disclosure describes example devices, systems, and techniques for accessing vasculature or another hollow anatomical structure of a patient of a patient. In some examples, devices described herein may be used as a fistula cannula to gain access to a fistula in the vascular system, such as during a hemodialysis procedure. In contrast to conventional devices, which may require two-handed operation or the assistance of a clinician for deployment, devices described herein may allow a patient to access vasculature without the assistance of a clinician, or by a single-handed operation. While the devices are primarily referred to herein as "vascular access devices," in other examples, the devices, systems, and techniques may be used to access other hollow anatomical structures of a patient. For example, in some examples, a hollow anatomical structure may include an arteriovenous (AV) graft, which may include a looped tube that connects an artery to a vein. As other examples, a hollow anatomical structure may include a vessel or a fistula in which a stent is deployed.

The vascular access devices described herein may be self-contained assemblies configured to be used for cannulation of a fistula, for example, self-cannulation. In some examples, a needle and a cannula of a device may be introduced into vasculature together, with the needle extending distally from the end of the cannula to facilitate introduction of the cannula into the vasculature. The needle may subsequently be retracted into a housing of the vascular access device to leave the cannula in the vasculature, with the cannula providing a structure through which fluid can be withdrawn from or introduced into the vasculature. In some examples, the vascular access device includes at least one needle guide configured to maintain the needle along a path substantially parallel to the needle guide as the needle is retracted through the cannula into a housing of the device. The at least one needle guide may help the needle retract into the housing in a predictable manner and reduce any adverse interactions between the needle and cannula during the retraction of the needle.

In some examples, a device including a housing defining a housing lumen extending from a housing proximal end to a housing distal end. The device further includes a cannula defining a cannula lumen extending from a cannula proximal end to a cannula distal end, and a needle configured to be locked in a deployed configuration in which the needle extends within the cannula lumen and protrudes from the cannula distal end. The cannula may be mechanically coupled to the housing distal end. The needle is configured to slide proximally through the cannula lumen from the deployed configuration into a retracted configuration in which at least a portion of the needle is within the housing lumen. The device further includes at least one needle guide in the housing lumen. The at least one needle guide is configured to maintain the needle along a path in the housing lumen substantially parallel to the needle guide when the needle moves between the deployed configuration and the retracted configuration.

In some examples, an example technique includes introducing at least a cannula distal end of a cannula and a needle protruding from the cannula distal end in a deployed configuration into a hollow anatomical structure of a patient. The cannula is mechanically coupled to a housing distal end of a housing defining a housing lumen. The cannula defines a cannula lumen extending from a cannula proximal end to the cannula distal end. The example technique further includes retracting the needle from the deployed configuration into a retracted configuration while leaving the cannula in the hollow anatomical structure. At least a portion of the needle is within the housing lumen in the retracted configuration. At least one needle guide in the housing lumen maintains the needle along a path in the housing lumen substantially parallel to the needle guide between the deployed configuration and the retracted configuration.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Reference is made to the attached drawings, wherein elements having the same reference numeral designations represent similar elements throughout and wherein.

DETAILED DESCRIPTION

Unless defined otherwise, all technical and scientific terms used generally have the same meaning as commonly understood by one of ordinary skill in the art.

The articles "a" and "an" are used to refer to one or to more than one (i.e., to at least one) of the grammatical object of the article. For example, "an element" means one element or over one element.

The term "at least" refers to no less than or at the minimum. For instance, "at least one" could be one or any numbers more than one.

In some examples, the term "biasing element" refers to an element capable of biasing another element with a biasing force applied in a predetermined direction.

In some examples, the term "cannula" refers to an elongated structure (e.g., a tubular member) defining a lumen capable of receiving another elongated element, for example a needle, or capable of receiving a fluid.

In some examples, the term "cap" refers to an element at an end of a housing of a device and coupled to a needle, and, in some cases, configured to help close the end of the device and cause the needle to retract in response to application of a force to the cap.

In some examples, the term "deployed configuration" refers to a configuration of a device in which at least a first portion of the device protrudes from another portion of the device and at least the first portion of the device is ready to be introduced into a tissue site, for example vasculature.

In some examples, the term "distal" refers to a direction toward a patient or a tissue site, or away from a clinician.

In some examples, the term "housing" refers to a hollow element or body having a lumen or chamber dimensioned to receive another element or assembly in the lumen or chamber.

In some examples, the term "knob" refers to an element secured to an end of a needle within a housing of a device.

In some examples, the term "needle" refers to a solid or hollow elongated member that defines an end configured to pierce, poke, enter, or otherwise be introduced into a substrate relatively softer than the needle, for example, tissue of a patient. The needle may include a sharp end to facilitate introduction of the end through tissue of a patient.

In some examples, the term "needle guide" refers to at least one elongated member configured to maintain or constrain a needle along a path substantially parallel to the elongated member as the needle is moved, for example, retracted into a housing.

In some examples, the term "proximal" refers to away from a patient or a tissue site, or towards a clinician.

In some examples, the term "retracted configuration" refers to a configuration of a device in which at least a portion of the device is retracted into a housing of the device relative to a deployed configuration.

In some examples, the term "unitary" refers to an integrated whole, for example, a monolithic element or combination of elements fabricated in a single seamless piece.

Devices such as catheters or cannulas may be used to gain access to a vascular system of a patient for hemodialysis or other procedures, or to gain access to other hollow anatomical structures in a patient. For example, cannulas may be used to access vasculature through a fistula. A fistula cannula may be introduced into a blood vessel of a patient with the aid of a needle, e.g., disposed within the cannula. In some examples, a vascular access device includes a housing defining a housing lumen, a cannula defining a cannula lumen, and a needle configured to be locked in a deployed configuration in which the needle extends within the cannula lumen and protrudes from a distal end of the cannula. The needle is configured to slide proximally through the cannula lumen from the deployed configuration into a retracted configuration in which at least a portion of the needle is within the housing lumen. The vascular access device includes at least one needle guide in the housing lumen. The at least one needle guide is configured to facilitate retraction of the needle by at least maintaining the needle along a path in the housing lumen substantially parallel to the needle guide when the needle moves between the deployed configuration and the retracted configuration. As discussed in further detail below, the at least one needle guide may reduce or prevent inadvertent movement of the needle in unintended directions during movement of the needle from the deployed configuration to the retracted configuration.

Some cannulas may require a multi-step operation to gain vascular access: a first step may include inserting the cannula and needle together into the vascular system while the needle is in the deployed configuration, and once access has been gained, a second step may include removing the needle from the cannula. The relatively soft or flexible cannula remains in place in the vascular system during the medical procedure. The vascular access devices described herein are configured to provide a self-contained assembly, such that when the needle is removed from the cannula, the needle is retracted into the device, thereby protecting a user from the sharp end of the needle and help prevent needle stick (e.g., inadvertent puncturing of the needle of a person or object). A device that is configured to retract a needle away from a blood vessel (or other hollow anatomical structure) of the patient in a controlled manner using the one or more needle guides may enable the relatively soft flexible cannula to both remain intact and remain in place in the blood vessel without the needle. This may provide more comfort to a patient compared to devices that leave the needle in vasculature for the duration of a dialysis session or other procedure. Leaving the soft flexible cannula in the blood vessel may also aid in the prevention of infiltration of the vessel wall. For example, unlike a needle, an unaided flexible cannula may not penetrate a vessel wall.

Conventional vascular access devices may require two hands or a clinician to cannulate and retract the needle. Further, conventional devices may include separate cannula and needle assemblies and may not be completely self-contained. Example devices, systems, and techniques according to the disclosure may help address the aforementioned shortcomings of conventional vascular access devices. For example, the devices and system described herein may enable a user to self-cannulate, for example, using one hand, to access the vasculature without the need for a clinician or a second person to facilitate vascular access. The example devices described herein may also facilitate the performance of some medical procedures in a domestic or other non-clinical environment, reducing or even eliminating the need for a patient to travel to a clinical location such as a dialysis center for treatment.

In some examples, an example technique may include introducing at least a cannula distal end of a cannula and a needle protruding from the cannula distal end in a deployed configuration into a hollow anatomical structure of a patient. The cannula is mechanically coupled to a housing distal end of a housing defining a housing lumen. The cannula defines a cannula lumen extending from a cannula proximal end to the cannula distal end. The example technique includes retracting the needle from the deployed configuration into a retracted configuration while leaving the cannula in the hollow anatomical structure. At least a portion of the needle is within the housing lumen in the retracted configuration. At least one needle guide in the housing lumen maintains the needle along a path in the housing lumen substantially parallel to the needle guide between the deployed configuration and the retracted configuration.

Figure 1:
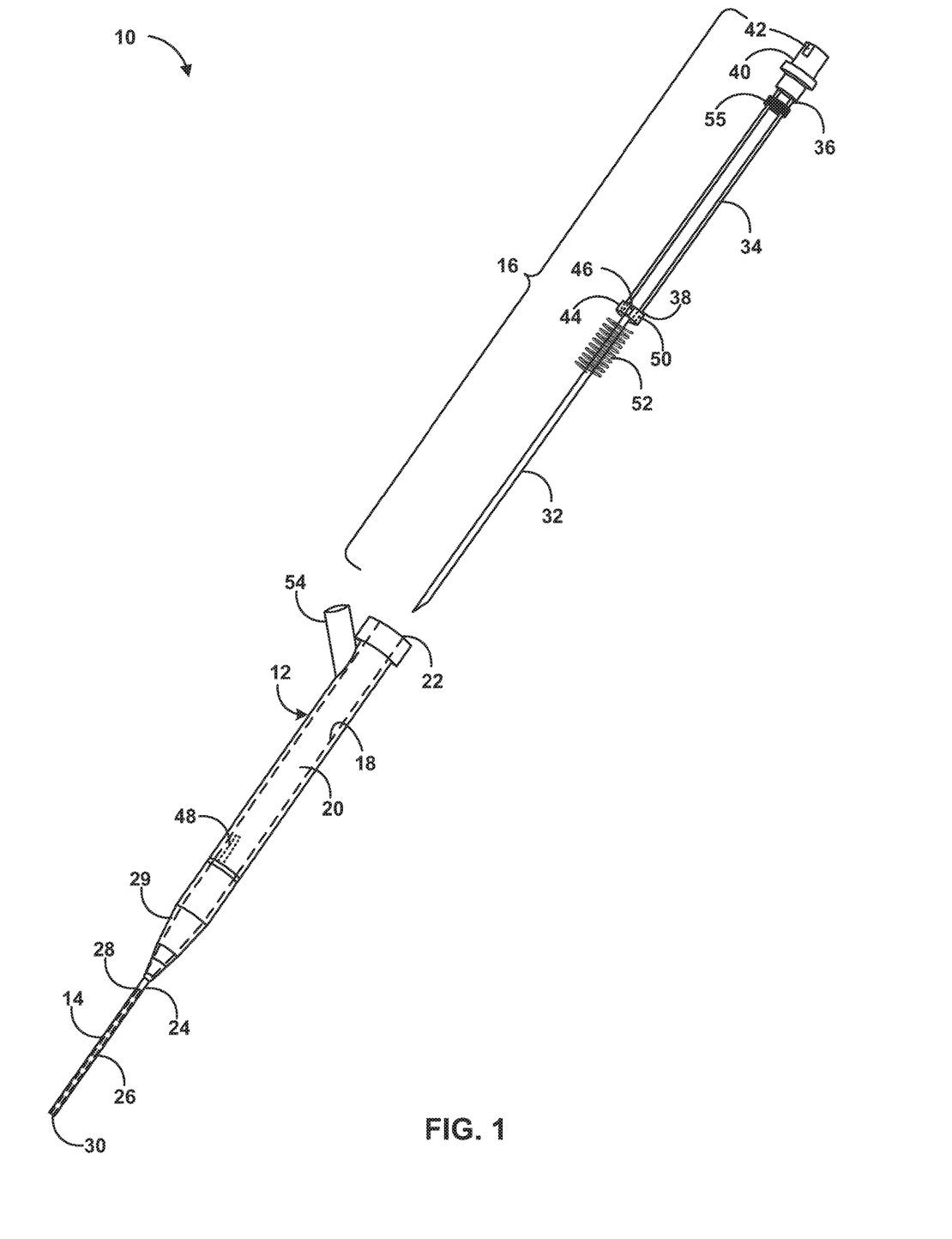
FIG. 1 is a schematic and conceptual exploded view illustration of an example device including a housing, a cannula, and a retractable needle assembly.

FIG. 1 is a schematic and conceptual exploded view illustration of an example device 10 including a housing 12, a cannula 14, and a retractable needle assembly 16. In some examples, a catheter, a cannulation device, or any other device for accessing vasculature may include example device 10. Thus, device 10 may also be referred to as a vascular access device. A user may use retractable needle assembly 16 to introduce cannula 14 into vasculature of a patient, subsequently retract needle assembly 16 to leave cannula 14 in the vasculature during the procedure, and then withdraw cannula 14 from the vasculature after the procedure. Retracting needle assembly 16 after introducing cannula 14 into the vasculature may provide improve patient comfort (relative to devices that leave a needle in the cannula and vasculature during a procedure), and reduce pain or adverse effects to a patient. Although vascular access is primarily referred to throughout the description of device 10, as well as other devices described herein, in other examples, the devices described herein and systems including such devices may be used to access another hollow anatomical structure of a patient, such as other organs.

Housing 12 is configured to house needle assembly 16. Housing 12 may be formed from any suitable material, for example, a rigid or semi-rigid material, and may include one or more of plastic, glass, metal, or alloy. In some examples, at least a portion of housing 12 may be substantially transparent or translucent, or define an optical window, so that a clinician or patient may observe an interior of housing 12, e.g., to confirm a blood vessel has been accessed based on the presence of flashback in housing 12. In addition to or instead of the transparent or translucent portion of housing 12, in some examples, at least one portion of housing 12 may be opaque.

Housing 12 has any suitable shape, such as, but not limited to a substantially cylindrical shape (e.g., cylindrical or cylindrical along a major portion of its mid-section). The shape of housing 12 may be selected to permit a user to grasp device 10 with one hand, introduce cannula 14 and needle assembly 16 into a hollow anatomical structure of the user while holding housing 12 with only one hand, and/or retract needle assembly 16 from cannula 12 while holding housing 12 with only one hand. In some examples, housing 12 may be provided with a cover or sleeve to facilitate gripping of housing 12 by a user. The sleeve may include any suitable material, for example, plastic, metal, glass, or alloy. In some examples, the cover or sleeve, or housing 12 itself, may define a surface texture to facilitate gripping and reduce or avoid slippage during deployment, use, retraction, and removal of device 10.

Housing 12 defines an inner surface 18, which defines a housing lumen 20 configured to receive needle assembly 16 and fluids, e.g., blood of a patient. Housing lumen 20 may extend from a housing proximal end 22 to a housing distal end 24 along a housing longitudinal axis extending through housing proximal end 22 and housing distal end 24. Housing 12 and housing lumen 20 may be provided with any suitable dimensions, for example, a length, diameter, cross-section, wall thickness, to house needle assembly 16, and to allow passage of fluids from vasculature through housing 12, e.g., to a tube connected to housing 12 at side port 54, at any suitable predetermined flow rates.

Housing lumen 20 may be fluidically coupled to cannula 14. Cannula 14 defines a cannula lumen 26, through which substances may be introduced into vasculature of a patient or through which substances may be removed from the vasculature. Cannula lumen 26 may extend from a cannula proximal end 28 to a cannula distal end 30 along a cannula longitudinal axis extending through cannula proximal end 28 and cannula distal end 30. In some examples, the cannula longitudinal axis may be substantially parallel, coaxial, or aligned with the housing longitudinal axis, for example, along a center of housing lumen 20. Cannula 14 may be mechanically coupled to housing 12, such as by welding (e.g., ultrasonic welding), an adhesive, a mechanical retention mechanism (e.g., interlocking or mating parts), or the like. In some examples, cannula proximal end 28 may be mechanically coupled to housing distal end 24. In some examples, cannula 14 is physically separate from housing 12 and mechanically connected thereto. In other examples, housing 12 and cannula 14 are integrally formed to define a unitary structure.

Cannula 14 may include any suitable material, for example, metal, alloy, or plastic. In some examples, cannula 14 is more flexible than housing 12. In some examples, cannula 14 includes a polymeric material for example, a plastic, a rubber, or an elastomer, that is sufficiently soft and flexible to minimize patient discomfort when cannula 14 is introduced into vasculature. In some examples, cannula 14 may not be sufficiently rigid or otherwise configured to penetrate patient tissue, and introduction of cannula 14 into vasculature may be facilitated by needle assembly 16.

Needle assembly 16 includes a needle 32. Needle 32 may be housed at least partly in housing 12, for example, in housing lumen 20, in the deployed and retracted configuration of needle 32. Needle 32 is configured to extend through cannula lumen 26 of cannula 14, for example, at least in, or only in, the deployed configuration, to facilitate introduction of cannula 14 into vasculature of a patient. Needle 32 may be formed of any suitable rigid material, for example, plastic, metal, or alloy. In some examples, needle 32 is more rigid than cannula 14, for example, sufficiently rigid to facilitate introduction of cannula 14 into vasculature. In some examples, cannula 14 may be more flexible or softer than needle 32, which may help increase patient comfort and reduce pain, discomfort, or adverse effects on the vasculature if device 10 or cannula 14 shifts or moves during cannulation or during a treatment or procedure.

Needle 32 is configured to be locked in a deployed configuration (described with reference to FIGS. 2A and 2B) in which needle 32 extends within cannula lumen 26 and protrudes from cannula distal end 30. Thus, needle 32 and cannula 14 may have any suitable respective lengths that enable a distal tip of needle 32 to extend distally past cannula distal end 30, and that enable needle 32 to be partly or completely housed within housing lumen 12 in a retracted configuration. In some examples, at least a portion of needle 32, for example, a proximal end or portion of needle 32, is within housing lumen 20 when needle 32 is in the deployed configuration. Needle 32 is configured to slide proximally through cannula lumen 26 from the deployed configuration into a retracted configuration (described with reference to FIGS. 3A and 3B) in which at least a portion of needle 32 is within housing lumen 20. For example, a distal end or tip of needle 32 may be within housing lumen 20 when needle 32 is in the retracted configuration.

Due to the locking of needle 32 in a deployed configuration and mechanical connection between needle 32 and cannula 14 by way of housing 12, in some examples, a patient may introduce cannula 14 and needle 32 into a fistula or other hollow anatomical structure of while grasping device 10 with only one hand (i.e., one hand operation of device 10 by a user). A user may keep his or her other hand on the cannula as the needle is being retracted or for another function. This may enable a patient to self-cannulate without the aid of a clinician or another person. Thus, device 10 may be used to perform a dialysis procedure at home without the needle to travel to a dialysis center for treatment.

Device 10 includes at least one needle guide 34, which is configured to help needle 32 predictably retract into housing 32 when needle 32 moves from the deployed configuration to the retracted configuration. Needle guide 34 may be in housing lumen 20, for example, in both the deployed and retracted configuration, or at least in the deployed configuration of needle 32. At least one needle guide 34 is configured to maintain needle 32 along a predetermined path in housing lumen 20 that is substantially parallel (e.g., parallel or nearly parallel to the extent permitted by manufacturing variances) to needle guide 34 when needle 32 moves between the deployed configuration and the retracted configuration. In some examples, the path may be along one or both of the housing longitudinal axis or the cannula longitudinal axis.

In some examples, at least one needle guide 34 may reduce or prevent inadvertent movement of needle 32 in unintended directions during movement of needle 32 from the deployed configuration to the retracted configuration. For example, at least one needle guide 34 may guide a movement of needle 32 such that movement of needle 32 towards or through a wall of cannula 14 may be reduced or avoided. At least one needle guide 34 may also provide structural connections or coupling between different elements of needle assembly 16, as described herein. In some examples, at least one needle guide 34 may help prevent needle 32 from blocking cannula lumen 26, or blocking a proximal inlet of cannula lumen 26, for example, by reducing or preventing a tilt or angular movement of needle 32 towards or into cannula lumen 26 in the retracted position.

At least one needle guide 34 may extend between a guide proximal end 36 and a guide distal end 38. In some examples, at least one needle guide 34 includes a rigid and substantially straight (e.g., straight or nearly straight to the extent permitted by manufacturing variances) elongated member extending from guide proximal end 36 to guide distal end 38, as shown in FIG. 1. In some example, at least one needle guide 34 includes two needle guides, as shown in FIG. 1. For example, at least one needle guide 34 may include at least two rigid and substantially straight elongated members that are substantially parallel (e.g., parallel or nearly parallel to the extent permitted by manufacturing variances) to each other. In other examples, at least one needle guide 34 may include more than two elongated members, such as three to six elongated members or more than six elongated members. One or more elongated members of the at least one needle guide 34 may include or act as rails extending along housing lumen 20, and the rails may guide movement of needle 32 between the deployed and retracted configurations. At least one needle guide 34 may include any suitable material, for example, metal, alloy, or plastic.

In some examples, an entirety of needle 32 is within housing lumen 20 when needle 32 in the retracted configuration. Housing entirety of needle 32 within housing lumen 20 in the retracted configuration may reduce or prevent needle sticks, for example, through a wall of cannula 14, during a treatment or procedure in which cannula 14 is introduced and left in vasculature to introduce fluids into or withdraw fluids from vasculature. For example, even if device 10 is moved, needle 32 may remain within housing lumen 20 in the retracted configuration, and avoid inadvertent piercing or entering a wall of cannula 14. Housing entirety of needle 32 within housing lumen 20 in the retracted configuration may also reduce or prevent needle 32 from contacting a user, for example a patient or a clinician, in case of movement of device 10 or a jerk or unexpected relative motion between device 10 and the patient or the clinician.

Needle assembly 16 may have any suitable configuration that includes at least one needle guide. In the example shown in FIG. 1, needle assembly 16 includes a cap 40 secured to needle 32, for example, at a proximal end of needle 32. Cap 40 is configured to rotate from a locked configuration in which needle 32 is maintained in the deployed configuration to an unlocked configuration in which needle 32 is configured to retract (into housing lumen 20) to the retracted configuration. For example, cap 40 may define a lever 42 configured to be engaged by a user (for example, a clinician or a patient) to cause cap 40 to rotate from the locked configuration to the unlocked configuration. In some examples, cap 40 is secured to needle 32 and is configured to rotate needle 32 as cap rotates 40 from the locked configuration to the unlocked configuration. For example, cap 40 may be secured to needle 32 by one or more needle guides of at least one needle guide 34, and rotating cap 40 may cause at least one needle guide 34 to rotate, ultimately causing needle 32 to rotate. Thus, at least one needle guide 34 may be configured to rotate in response to rotation of cap 40.

The automatic retraction of needle 32 into housing lumen 20 by actuation (e.g., rotation) of cap 40 may enable a user to retract needle 32 into housing lumen 20 while holding device 10 with only one hand (i.e., one hand operation of device 10 by a user). A user may keep his or her other hand on the cannula as the needle is being retracted or for another function. This may enable a patient to self-cannulate without the aid of a clinician or another person. This provides another mechanism by which a patient may use device 10 to perform a dialysis procedure at home without the needle to travel to a dialysis center for treatment.

Cap 40 may be formed from any suitable material, for example, metal, alloy, or plastic. In some examples, cap 40 and at least one needle guide 34 are a unitary structure. In some examples, cap 40 and one or both of needle guide 34 and knob 44 are a unitary structure or otherwise integrated together. In other examples, cap 40 and at least one needle guide 34 are physically separate structures. Cap 40 or at least one needle guide 34 may be directly attached or secured to needle 32, or may be attached or secured to needle 32 via another element of device 10. For example, device 10 may further include a knob 44 secured to a needle proximal end of needle 32. The knob may have a larger cross-sectional size than that of needle 32 in a direction normal to the housing longitudinal axis. Knob 44 may be configured to maintain needle 32 in a deployed configuration and to enable needle 32 to retract into the retracted configuration. For example, knob 44 may define a channel 46, and inner surface 18 of housing 12 may define an elongated key 48 configured to slide through channel 46. In some examples, elongated key 48 may be dimensioned to slide snugly through channel 46, or dimensioned to be narrower than channel 46 to slide through channel 46.

In some examples, knob 44 defines at least one guide lumen 50, configured to receive at least a portion (e.g., an elongate member) of needle guide 34. At least one needle guide 34 may be configured to extend through at least one guide lumen 50, for example, in one or both of the deployed and retracted configuration of needle 32. For example, at least one guide lumen 50 may be configured to enable knob 44 to slide along needle guide 34 as needle 32 moves from the deployed configuration to the retracted configuration. Without guide lumen 50, knob 44 may get hung up on the distal end of at least one needle guide 34, which may prevent needle 32 from readily moving from the deployed configuration to the retracted configuration. In some examples, at least one guide lumen 50 is dimensioned to slide snugly along at least one guide needle 34. In other examples, at least one guide lumen 50 is dimensioned to be wider than at least one needle guide 34 to slide over at least one guide needle 34. In some examples, the number of lumens of at least one guide lumen 50 may be the same as the number of elongated members of at least one needle guide 34, and each elongated member of at least one needle guide 34 may slide through a respective lumen of at least one guide lumen 50.

Device 10 includes a biasing element 52 configured to bias needle 32 away from the deployed configuration to the retracted configuration. Biasing element 52 may include any suitable structure that is configured to apply a force to needle 32 to bias needle 32 towards the retracted position. For example, biasing element 52 can include at least one of a spring, a magnet, a pressure chamber, or a chemical expansion chamber. In some examples, the at least one spring may include a compression spring, a tension spring, a helical spring, a leaf spring, or a torsion spring or any combinations thereof. Biasing element 52 may be formed from a composition including one or more of plastic, rubber, metal, or alloy, or any suitable resilient material. In the example shown in FIG. 1, biasing element 52 includes a spring. In other examples, biasing element 52 may include multiple members, for example, multiple springs, or multiple types of biasing elements. In some examples, biasing element 52 may be configured to bias needle 32 toward the deployed configuration, for example, by applying a distal biasing force on needle 32. In some such examples, a user may release the biasing force to cause needle 32 to retract into the retracted configuration. For example, instead of "pushing" needle 32 proximally to cause retracting, biasing element may "pull" needle 32 proximally to cause retraction. In some examples, biasing element 52 may be located proximal to needle 32, and pull needle 32 proximally toward cap 40 to cause needle 32 to retract.

In examples in which biasing element 52 includes a pressure chamber, the pressure chamber may include a pressurized fluid locked in a compressed configuration. A user may rotate or plunge cap 40 which may cause the pressure chamber to be unlocked, resulting in expansion of the fluid. The tendency of the pressurized fluid to expand may bias needle 32 away from the deployed configuration to the retracted configuration. In examples in which biasing element 52 includes a chemical expansion chamber, the chemical expansion chamber may include two or more isolated compositions that generate a volumetrically expanding product by chemical reaction when combined. For example, a user may rotate or plunge cap 40 which may be connected to the chemical expansion chamber to pierce a structure (e.g., a membrane or container) holding the two or more compositions in isolation, resulting in mixing and chemical reaction between the two or more compositions. The chemical reaction may result in expansion of the chemical expansion chamber, causing needle 32 to be biased away from the deployed configuration into the retracted configuration.

As discussed above, housing lumen 20 is configured to receive a fluid. In some examples, to help maintain the fluid within housing lumen 20 when device 10 is assembled, device 10 includes a seal 55 between cap 40 and knob 44. Seal 55 may include, for example, a gasket, or an o-ring. Seal 55 may include any suitable sealing material, for example, one or more of plastic, rubber, elastomer, metal, or alloy. Seal 55 may reduce or prevent flow of fluid past knob 44 or otherwise across cap 40.

In some examples, cannula 14 and housing lumen 20 are fluidically connected at least when needle 32 is in the retracted configuration to allow passage of a fluid from cannula lumen 26 to housing lumen 20. In some examples, housing 12 defines a side port 54 fluidically connected to housing lumen 20. Thus, side port 54 may be fluidically connected through housing lumen 20 to cannula lumen 26 and to cannula distal end 30. In some examples, device 10 may include an antireflux valve, for example, if a tube (such as a blood line) is not attached to side port 54.

Elements of device 10 or needle assembly 16 may be formed from one or more of any suitable materials described herein, for example, glass, metal, alloy, or polymeric material. In some examples, entire needle assembly 16 may be formed of substantially the same type of material, for example, a polymeric material or a particular type of polymeric material, or entirely made of metal or alloy. In other examples, different elements of device 10 or needle assembly 16 may be formed of different materials.

Device 10 may initially be configured such that needle 32 is in a deployed configuration. This may also be referred to as a deployed configuration of device 10. For example, device 10 may be fabricated or manufactured to initially be in a deployed configuration, in which at least a distal tip of needle 32 extends distally past distal end 30 of cannula 14. A clinician or a patient may introduce a portion of device 10 (for example, cannula 14 and needle 32) into a vasculature while needle 32 is in the deployed configuration. The clinician or patient may then subsequently cause needle 32 to retract into a retracted configuration while cannula 14 remains in the vasculature during a procedure. After the procedure is complete, the clinician or patient may withdraw device 10 (for example, cannula 14) from the vasculature, as described with reference to FIGS. 2A to 6C.

Figures 2A, 2B:
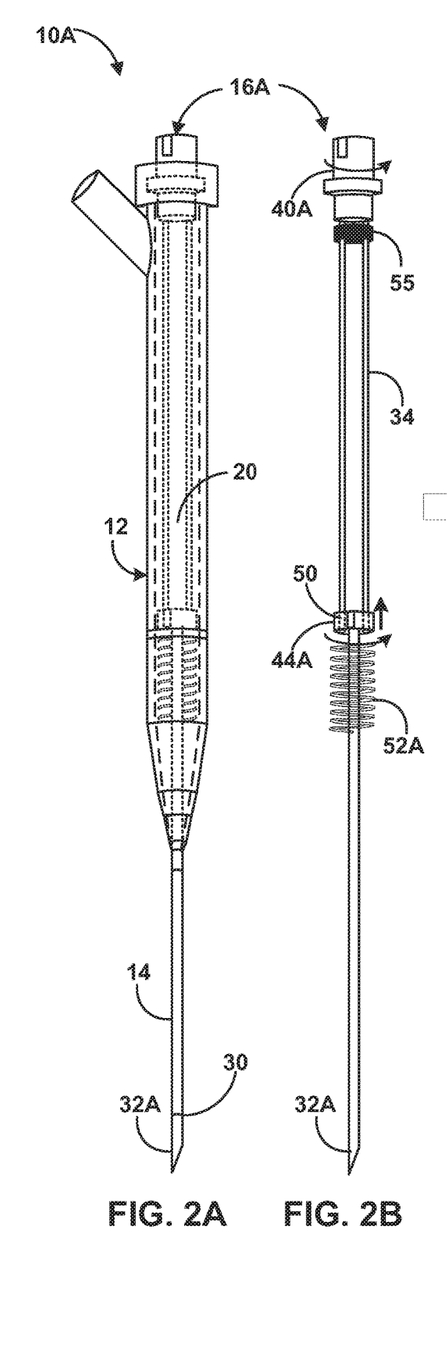
FIG. 2A is a schematic and conceptual illustration of the device of FIG. 1 in a deployed configuration.
FIG. 2B is a schematic and conceptual illustration of the needle assembly of FIG. 2A in a deployed configuration.

FIG. 2A is a schematic and conceptual illustration of device 10 of FIG. 1 in a deployed configuration 10A. Like elements of device 10 of FIG. 1 are numbered alike in FIG. 2A, and further labeled "A" to denote the deployed configuration of elements of device 10. For example, FIG. 2B is a schematic and conceptual illustration of needle assembly 16 in a deployed configuration 16A. In the deployed configuration 10A of device 10 shown in FIG. 2A, needle assembly 16 may maintain a deployed configuration 16A. For example, cap 40A may be positioned to lock needle 32 in a locked configuration 32A, so that a distal end of needle 32A protrudes through and distally past cannula distal end 30. In some examples, in deployed configuration 16A, cap 40A may maintain knob 44A in a locked configuration, preventing needle 32 from retracting into housing 12. In the locked configuration, knob 44A may be spaced from cap 40A, for example, along housing lumen 20. In the deployed configuration 10A, biasing element 52 may be primed to expand or otherwise apply a biasing force to bias needle 32 proximally towards housing 12 away from cannula 14. Thus, in an unlocked configuration, biasing element 52 may cause needle 32 to proximally retract away from cannula 14 into housing lumen 20 of housing 12.

Figure 3A:
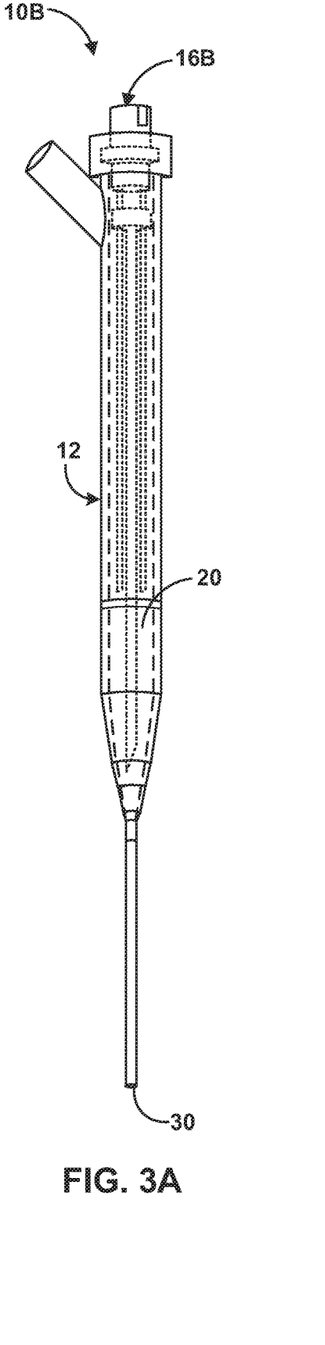
FIG. 3A is a schematic and conceptual illustration of the device of FIG. 1 in a retracted configuration.
Figure 3B:
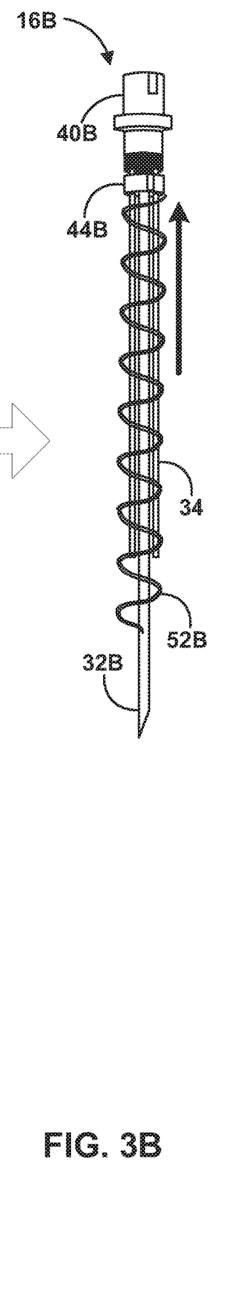
FIG. 3B is a schematic and conceptual illustration of the needle assembly of FIG. 2B in a retracted configuration.

FIG. 3A is a schematic and conceptual illustration of device 10 of FIG. 1 in a retracted configuration 10B. Like elements of device 10 of FIG. 1 are numbered alike in FIG. 3A, and further labeled "B" to denote the retracted configuration of elements of device 10. For example, FIG. 3B is a schematic and conceptual illustration of needle assembly 16 in a retracted configuration 16B. As shown in FIG. 3B, in some examples, biasing element 52B in the retracted configuration may maintain needle 32 in retracted configuration 32B, for example, preventing needle 32 from returning to cannula 14 or otherwise into vasculature. In the retracted configuration, knob 44B may be closer to cap 40B than in the deployed configuration. For example, knob 44B may directly contact a surface of cap 40B in housing lumen 20, or contact cap 40B via seal 55. In some examples, space between knob 44B and cap 40B in housing lumen 20 may be substantially minimal or eliminated in the retracted configuration. In some examples, device 10 may irreversibly transition from deployed configuration 10A to retracted configuration 10B, such that the user is prevented from returning device 10 from the retracted configuration 10B to deployed configuration 10A. Such an irreversible transition may reduce or avoid inadvertent needle sticks and/or unintended introduction of needle 32 into vasculature or other tissue of the patient or clinician, for example, after device 10 is used and withdrawn from a region of the patient.

Figure 4A:
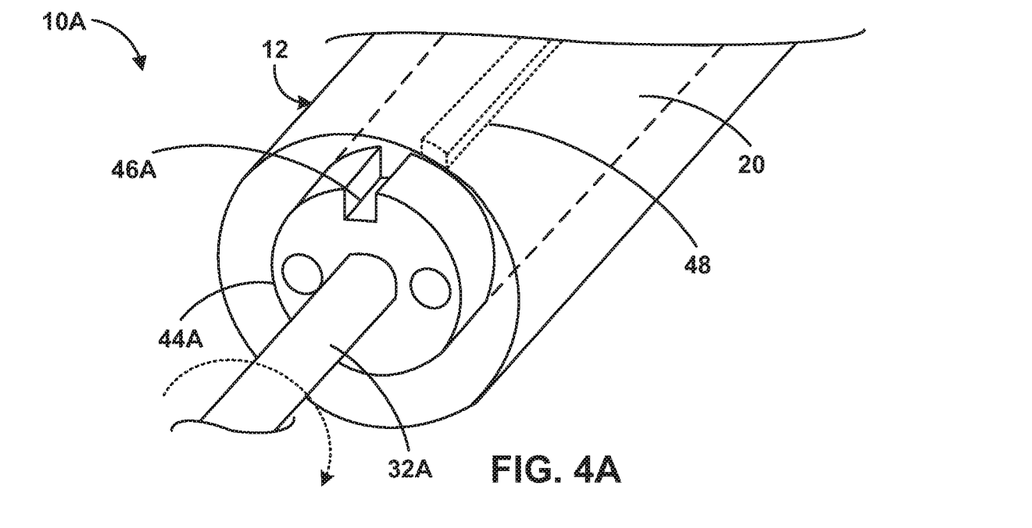
FIG. 4A is a schematic and conceptual illustration of a partial view of an example deployed configuration of the device of FIG. 1.

FIG. 4A is a schematic and conceptual illustration of a partial view of deployed configuration 10A of device 10 of FIG. 1. In some examples, in deployed configuration 10A, knob 44A is rotated relative to elongated key 48 so that elongated key 48 is misaligned with channel 46A defined by knob 44A. For example, channel 46A and elongated key 48 may be misaligned to prevent knob 44A (and channel 46A) from sliding along elongated key 48 and to prevent knob 44a from moving through housing lumen 20 and retracting needle 32 from cannula 14. In the deployed configuration 10A, an end, for example, a distal end, of elongated key 48, may abut a surface of knob 44A to prevent knob 44A from moving proximally. Thus, elongated key 48 may lock and maintain knob 44A and needle 32A in the deployed configuration 10A indefinitely, or until a user triggers retraction of needle 32A.

Figure 4B:
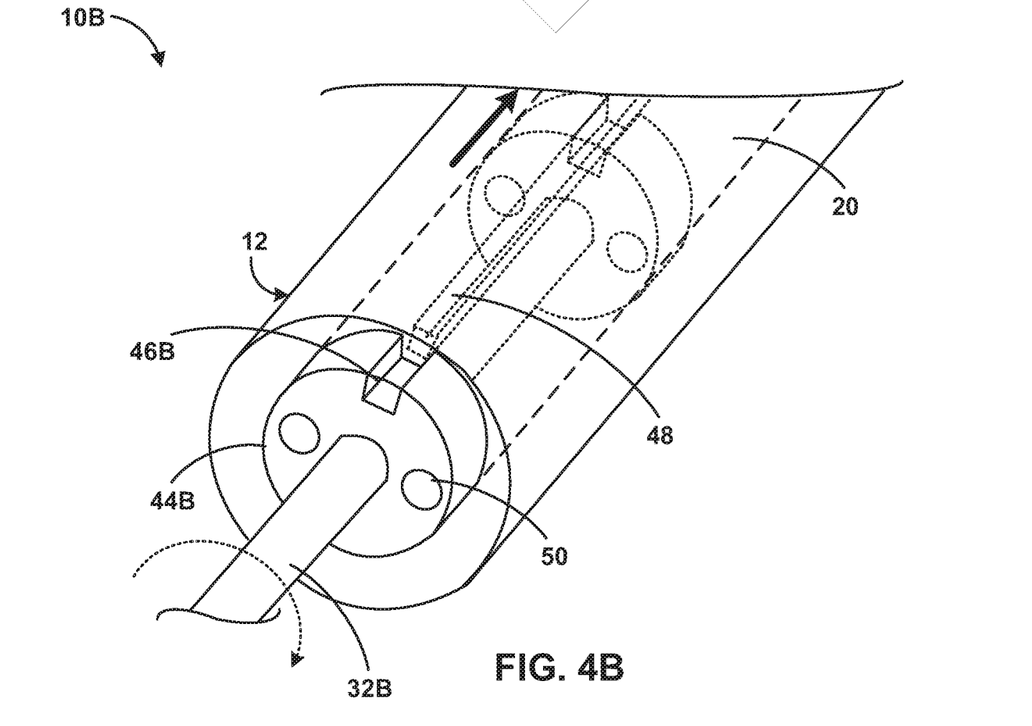
FIG. 4B is a schematic and conceptual illustration of a partial view of a retracted configuration of the device of FIG. 1.

FIG. 4B is a schematic and conceptual illustration of a partial view of retracted configuration 10B of device 10 of FIG. 1. A user, for example, a clinician or patient, may cause retraction of needle assembly 16 to transition device 10 from deployed configuration 10A to retracted configuration 10B. In some examples, a user may rotate cap 40 into rotated configuration 40B to cause needle 32 to rotate into rotated configuration 32B. Rotated cap 40B may rotate at least one needle guide 34 (not shown in FIGS. 4A and 4B) and knob 44 from deployed configuration 44A to retracted configuration 44B. In such an unlocked configuration 44B, channel 46B defined by knob 44B and elongated key 48 are aligned, enabling elongated key 48 to slide through channel 46B, and allowing knob 44B to move through housing lumen 20 along at least one needle guide 34 and retract needle 32A proximally into housing lumen 20.

In some examples, elongated key 48 may itself act as a needle guide, in addition to, or instead of, at least one needle guide 34. For example, elongated key 48 may extend along inner surface 18 of housing 12, so that elongated key 48 holds knob 44B (and therefore, needle 32B) in substantially the same rotational orientation (i.e., the same rotational position relative to a longitudinal axis of housing lumen 20) as knob 44B and needle 32B retract proximally along housing lumen 20. Further, while a single elongated key 48 is shown in the examples of FIGS. 2A to 4B, device 10 may include two or more elongated keys 48, for example, about a periphery of knob 44B, which may hold knob 44B in the same rotational orientation as knob 44B and needle 32B retract proximally along housing lumen 20. Thus, in some examples, elongated key 48 may maintain or help maintain needle 32B along a path substantially parallel to one or both of the cannula longitudinal axis or the housing longitudinal axis.

Figure 5:
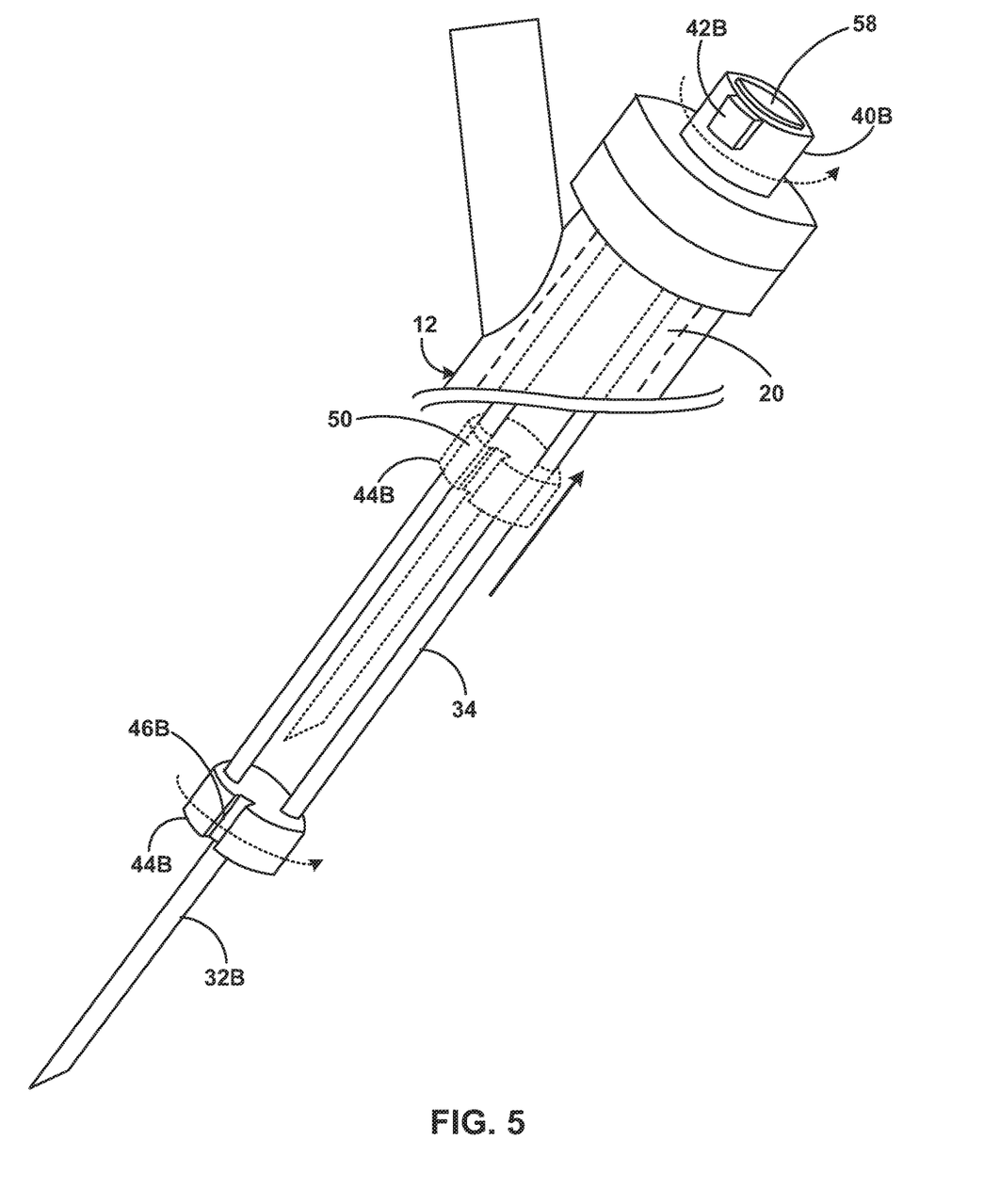
FIG. 5 is a schematic and conceptual illustration of a partial view of the device of FIG. 1 showing movement of the needle along the needle guides to assume the retracted configuration.

FIG. 5 is a schematic and conceptual illustration of a partial view of the device of FIG. 1 showing movement of needle 32 along the at least one needle guide 34 to assume retracted configuration 32B. As shown in FIG. 5, in some examples, in retracted configuration 10B of device 10, knob 44B may be aligned with elongated key 48 (not shown in FIG. 5), and slide proximally along at least one needle guide 34 towards cap 40, causing needle 32B to slide proximally into housing lumen 20. At least one guide lumen 50 of knob 44B may facilitate movement of knob 44B and needle 32B along at least one guide 34.

In some examples, cap 40 defines an air bleed opening to allow air (or another gas) that may be present in housing lumen 20 to escape, enabling fluid to be drawn into housing lumen 20. Device 10 may further include an air bleed membrane 58 covering the air bleed opening. Air bleed membrane 58 may be configured to permit flow of air through the air bleed opening while substantially preventing flow of liquids through the air bleed opening. In some examples, air bleed membrane 58 includes a polymeric material. In some examples, air bleed membrane 58 defines pores dimensioned to allow air to pass through air bleed membrane while preventing passage of liquids through air bleed membrane 58.

The use of device 10 to access vasculature is described with reference to FIGS. 6A to 6C and example techniques described with reference to FIG. 7.

Figures 6A, 6B:
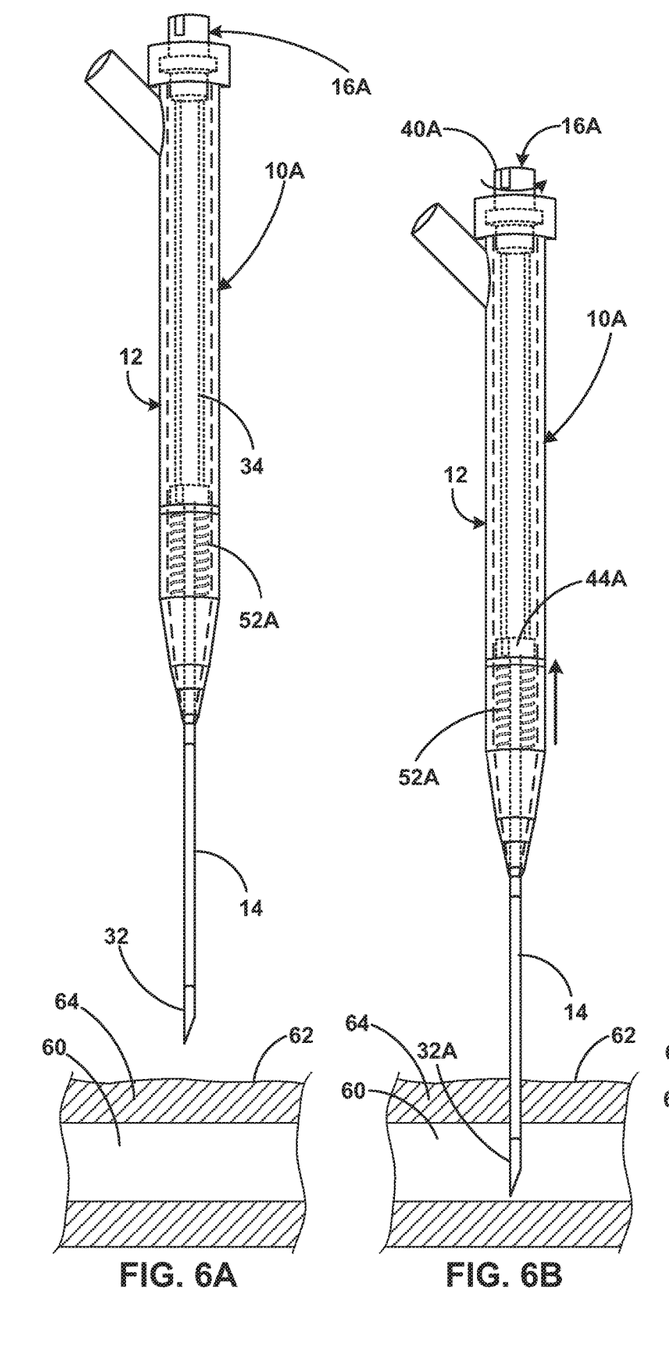
FIG. 6A is a schematic and conceptual illustration of the device of FIG. 1 in a deployed configuration prior to introduction in a blood vessel.
FIG. 6B is a schematic and conceptual illustration of the device of FIG. 1 in a deployed configuration during introduction in a blood vessel.
Figure 6C:
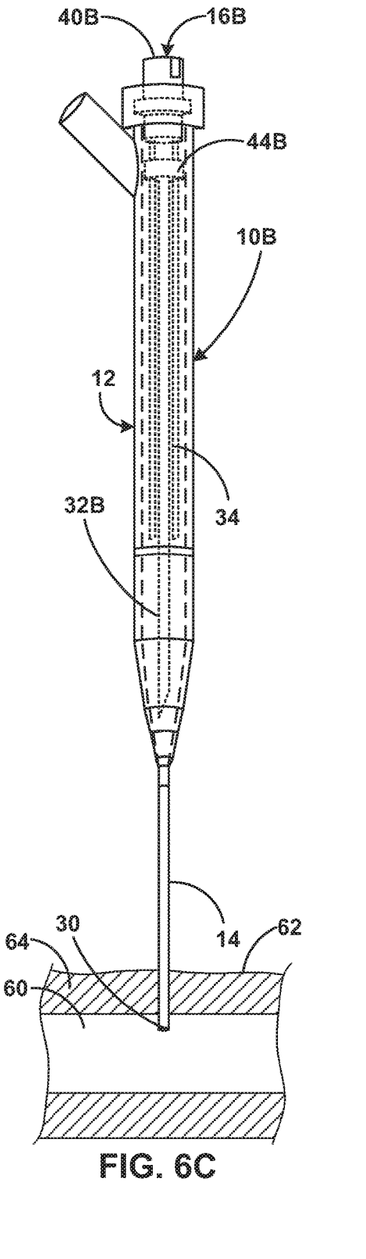
FIG. 6C is a schematic and conceptual illustration of the device of FIG. 1 in a retracted configuration with a cannula in a blood vessel.

FIG. 6A is a schematic and conceptual illustration of device 10 of FIG. 1 in deployed configuration 10A prior to introduction in a lumen 60 of a hollow anatomical structure of a patient. The hollow anatomical structure may include a blood vessel, or an artificial structure fluidically connected to a blood vessel. In some examples, the hollow anatomical structure includes an arteriovenous fistula. Thus, lumen 60 may not be defined by vasculature, and may instead be defined by a natural or artificial fistula fluidically connected to vasculature. For example, a natural fistula may be formed from tissue of a patient. An artificial fistula may be formed of a biocompatible polymeric material, or any suitable material. In some examples, the fistula may extend the vasculature to allow fluid to be introduced or removed via the fistula, reducing or avoiding repeated introduction of cannula 14 or needle 32 in tissue of patient. Lumen 60 may be at or adjacent a surface 62 of a patient tissue. For example, skin may define surface 62, and material 64 adjacent surface 62 may define lumen 60. Material 60 may include the natural or artificial fistula.

A user may bring device 10 in deployed configuration 10A in close proximity to surface 62, as shown in FIG. 6A, and may introduce needle 32 in locked or deployed configuration 32A within cannula 14 into lumen 60, as shown in FIG. 6B. FIG. 6B is a schematic and conceptual illustration of device 10 of FIG. 1 in deployed configuration 10A during introduction in a lumen of vasculature. The user may maintain device 10 in lumen 60 in deployed configuration only for a relatively short period of time, for example, to confirm proper placement and introduction of cannula 14 into a given region. In some examples, proper placement and introduction may be confirmed based on an observation of flashback into housing lumen 20, for example, through a transparent or translucent optical window of housing 12, or otherwise through a wall of housing 12. In some examples, the user may remove device 10A in the deployed configuration 10A from tissue of the patient and reintroduce device 10 in the deployed configuration 10A at another tissue site, for example, to seek a suitable site for introduction of cannula 14 along lumen 60.

After cannula 14 is placed at a suitable site, the user may retract needle 32. FIG. 6C is a schematic and conceptual illustration of device 10 of FIG. 1 in retracted configuration 10B with a cannula in lumen 60 of a hollow anatomical structure of the patient. The user may initiate retraction of needle 32 from cannula 14 by rotating cap 40A to retracted configuration 40B, ultimately causing needle 32 to be unlocked and move from deployed configuration 32A in which a distal tip of needle 32 protrudes from cannula distal end 30 to retracted configuration 32B in which the distal tip of needle 32 is contained within housing 12, as shown in FIG. 6C. In some examples, as shown in FIG. 6C, needle 32 may be fully contained within housing 12 when needle 32 is in the retracted configuration 32*b*. The user may leave cannula 14 in lumen 60 for a medical procedure, for example, introduce fluid into lumen 60 or withdraw fluid from lumen 60 via housing lumen 20 (for example, through side port 54). After the treatment or procedure is complete, the user may move device 10 away from surface 62, to cause cannula 14 to be withdrawn from lumen 60. The user may subsequently discard device 10, or sterilize device 10.

Figure 7:
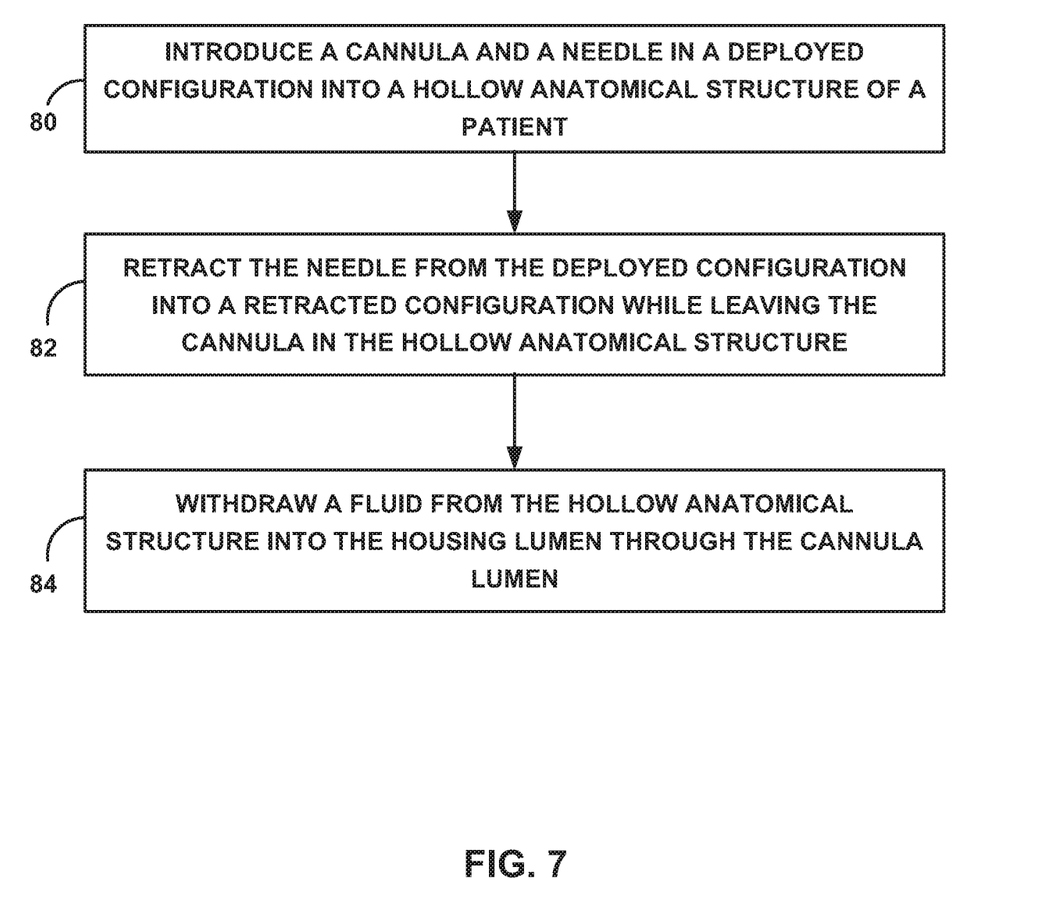
FIG. 7 is a flow diagram illustrating an example technique for introducing a cannula into vasculature.

FIG. 7 is a flow diagram illustrating an example technique for introducing cannula 14 into vasculature. In some examples, the example technique includes introducing cannula 14 and needle 32 in deployed configuration 10A into a hollow anatomical structure of a patient (80). For example, the hollow anatomical structure may include lumen 60 described with reference to FIGS. 6A to 6C. The example technique further includes retracting needle 32 from deployed configuration 10A into retracted configuration 10B, while leaving cannula 14 in the hollow anatomical structure (82). In some examples, in the retracted configuration 10B, substantially the entire needle 32 may be housed by housing 12, and no portion of needle 32 may remain in cannula 14. In some examples, cannula 14 may be soft or flexible, and while cannula 14 may initially be in a straight configuration during the introducing (80), cannula 14 may have a bent or non-linear configuration after the retracting (82).

The example technique of FIG. 7 may optionally include, after needle 32 is retracted into housing 12 (82), withdrawing a fluid from the hollow anatomical structure into housing lumen 20 through cannula lumen 26 (84). The fluid may optionally ultimately be withdrawn from side port 54 from housing lumen 20. In some examples, instead of or in addition to the withdrawing (84), the example technique of FIG. 7 may include delivering fluid through housing lumen 20 and through cannula lumen 26 into the hollow anatomical structure. In some examples, the example technique of FIG. 7 may be used to conduct dialysis.

In some examples, devices and techniques according to the disclosure may allow treatment at home or another preferred location, reducing or avoiding the need to travel, for example, to a clinical location, for treatment.

Various examples have been described. These and other examples are within the scope of the following claims.

What is claimed is:

1. A device comprising:
   a housing defining a housing lumen extending from a housing proximal end to a housing distal end;
   a cannula defining a cannula lumen extending from a cannula proximal end to a cannula distal end, the cannula being mechanically coupled to the housing distal end;
   a needle configured to be locked in a deployed configuration in which the needle extends within the cannula lumen and protrudes from the cannula distal end, the needle being configured to slide proximally relative to the housing distal end through the cannula lumen from the deployed configuration into a retracted configuration in which at least a portion of the needle is within the housing lumen; and
   at least one needle guide in the housing lumen, wherein the at least one needle guide is configured to maintain the needle along a path in the housing lumen substantially parallel to the needle guide as the needle moves between the deployed configuration and the retracted configuration.

2. The device of claim 1, wherein the at least one needle guide extends between a guide proximal end and a guide distal end, the at least one needle guide comprising a rigid and substantially straight elongated member extending from the guide proximal end to the guide distal end.

3. The device of claim 2, wherein the at least one needle guide comprises at least two rigid and substantially straight elongated members.

4. The device of claim 1, further comprising a cap secured to the needle, wherein the cap is at the housing proximal end, wherein the cap is configured to rotate from a locked configuration in which the needle is maintained in the deployed configuration to an unlocked configuration in which the needle is configured to retract to the retracted configuration.

5. The device of claim 4, wherein the cap defines a lever configured to be engaged by a user to cause the cap to rotate from the locked configuration to the unlocked configuration.

6. The device of claim 4, wherein the cap is secured to the needle and is configured to rotate the needle as the cap rotates from the locked configuration to the unlocked configuration.

7. The device of claim 4, further comprising a knob secured to a needle proximal end of the needle, wherein the knob has a larger cross-sectional size than the needle.

8. The device of claim 7, wherein the knob defines a channel, and wherein an inner surface of the housing defines an elongated key configured to slide through the channel, and wherein, in the locked configuration, the channel and the key are misaligned to prevent the key from sliding through the channel and to prevent the knob from moving through the housing lumen, and wherein, in the unlocked configuration, the channel and the key are aligned to enable the key to slide through the channel and to allow the knob to move through the housing lumen.

9. The device of claim 7, wherein the cap is fixed to the at least one needle guide, and wherein the at least one needle guide is configured to rotate in response to rotation of the cap.

10. The device of claim 9, wherein the knob defines at least one guide lumen, wherein the at least one needle guide extends through the at least one guide lumen, and wherein the at least one guide lumen is configured to allow the knob to slide along the at least needle guide to cause the needle to move from the deployed configuration to the retracted configuration.

11. The device of claim 4, wherein the cap and the at least one needle guide are a unitary structure.

12. The device of claim 4, wherein the cap and the at least one needle guide are physically separate structures.

13. The device of claim 1, wherein the cannula is more flexible than the housing.

14. The device of claim 1, further comprising a biasing element configured to bias the needle away from the deployed configuration to the retracted configuration.

15. The device of claim 14, wherein the biasing element comprises at least one of a spring, a magnet, a pressure chamber, or a chemical expansion chamber.

16. The device of claim 1, further comprising a cap secured to the needle, wherein the cap is configured to rotate from a locked configuration in which the needle is maintained in the deployed configuration to an unlocked configuration in which the needle is configured to retract to the retracted configuration, wherein the cap defines an air bleed opening, the device further comprising an air bleed membrane covering the air bleed opening, wherein the air bleed membrane is configured to permit flow of air through the air bleed opening while substantially preventing flow of liquids through the air bleed opening.

17. The device of claim 1, wherein the housing defines a side port fluidically connected to the housing lumen.

18. The device of claim 1, wherein the cannula and the housing lumen are fluidically connected when the needle is in the retracted configuration to allow passage of a fluid from the cannula lumen to the housing lumen.

19. The device of claim 1, wherein the needle comprises a metal or an alloy.

20. The device of claim 1, wherein an entirety of the needle is within the housing lumen when the needle is in the retracted configuration.

21. The device of claim 1, wherein the at least one needle guide is in the housing lumen when the needle is in the deployed configuration and when the needle is in the retracted configuration.

22. The device of claim 4, wherein the cap is at a proximal end of the at least one needle guide.

23. A method comprising:
introducing at least a cannula distal end of a cannula and a needle protruding from the cannula distal end in a deployed configuration into a hollow anatomical structure of a patient, wherein the cannula is mechanically coupled to a housing distal end of a housing defining a housing lumen, and wherein the cannula defines a cannula lumen extending from a cannula proximal end to the cannula distal end; and
retracting the needle from the deployed configuration into a retracted configuration by at least sliding the needle proximally relative to the housing distal end through the cannula lumen while leaving the cannula in the hollow anatomical structure, wherein at least a portion of the needle is within the housing lumen when the needle is in the retracted configuration, and wherein at least one needle guide in the housing lumen maintains the needle along a path in the housing lumen substantially parallel to the needle guide as the needle moves between the deployed configuration and the retracted configuration.

24. The method of claim 23, wherein the hollow anatomical structure comprises an arteriovenous fistula.

25. The method of claim 23, wherein the hollow anatomical structure comprises a blood vessel.

26. The method of claim 23, further comprising withdrawing a fluid from the hollow anatomical structure into the housing lumen through the cannula lumen.

27. The method of claim 23, wherein retracting the needle comprises rotating a cap from a locked configuration in which the needle is maintained in the deployed configuration to an unlocked configuration in which the needle retracts to the retracted configuration, the cap being secured to the needle.

28. The method of claim 27, wherein rotating the cap comprises applying torque to a lever defined by the cap.

29. The method of claim 27, wherein rotating the cap causes a knob secured to a needle proximal end of the needle to twist from the locked configuration to the unlocked configuration.

30. The method of claim 23, wherein retracting the needle comprises exerting a biasing force by a biasing element on the needle to cause the needle to retract from the deployed configuration to the retracted configuration.

31. The method of claim 23, wherein retracting the needle from the deployed configuration into the retracted configuration while leaving the cannula in the hollow anatomical structure comprises retracting the needle while holding a device including the needle, the cannula in only one hand.

32. A device comprising:
a housing defining a housing lumen extending from a housing proximal end to a housing distal end;
a cannula defining a cannula lumen extending from a cannula proximal end to a cannula distal end, the cannula being mechanically coupled to the housing distal end;
a needle configured to be locked in a deployed configuration in which the needle extends within the cannula lumen and protrudes from the cannula distal end, the needle being configured to slide proximally relative to the housing distal end through the cannula lumen from the deployed configuration into a retracted configuration in which at least a portion of the needle is within the housing lumen;
at least one needle guide in the housing lumen, wherein the at least one needle guide is configured to maintain the needle along a path in the housing lumen substantially parallel to the needle guide as the needle moves between the deployed configuration and the retracted configuration; and
a cap secured to the needle, wherein the cap is configured to rotate from a locked configuration in which the needle is maintained in the deployed configuration to an unlocked configuration in which the needle is configured to retract to the retracted configuration.

* * * * *